US008246351B2

(12) United States Patent
Huang

(10) Patent No.: US 8,246,351 B2
(45) Date of Patent: Aug. 21, 2012

(54) POSITIONING METHOD FOR ORTHODONTIC APPLIANCE AND STRUCTURE THEREOF

(76) Inventor: Cheng-Ho Huang, Sanchong (TW)

( * ) Notice: Subject to any disclaimer, the term of this patent is extended or adjusted under 35 U.S.C. 154(b) by 36 days.

(21) Appl. No.: 12/859,999

(22) Filed: Aug. 20, 2010

(65) Prior Publication Data

US 2011/0159452 A1 Jun. 30, 2011

(30) Foreign Application Priority Data

Dec. 31, 2009 (TW) .............................. 98146128 A

(51) Int. Cl.
*A61C 7/16* (2006.01)
(52) U.S. Cl. ............................................. 433/24; 433/9
(58) Field of Classification Search ................... 433/8, 9, 433/24, 2
See application file for complete search history.

(56) References Cited

U.S. PATENT DOCUMENTS

| 3,738,005 | A | * | 6/1973 | Cohen et al. ....................... 433/3 |
| 4,360,341 | A | * | 11/1982 | Dellinger ......................... 433/24 |
| 4,551,096 | A | * | 11/1985 | Dellinger ......................... 433/24 |
| 4,626,208 | A | * | 12/1986 | Hall .................................. 433/3 |
| 4,657,508 | A | * | 4/1987 | Dellinger ......................... 433/24 |
| 5,971,754 | A | * | 10/1999 | Sondhi et al. ................... 433/24 |
| 6,123,544 | A | * | 9/2000 | Cleary ............................. 433/24 |
| 6,913,461 | B2 | * | 7/2005 | Gittleman ....................... 433/38 |
| 2004/0157184 | A1 | * | 8/2004 | Reising ............................. 433/8 |
| 2008/0227050 | A1 | * | 9/2008 | Marshall ......................... 433/24 |

* cited by examiner

*Primary Examiner* — Todd Manahan
*Assistant Examiner* — Michael R Ballinger
(74) *Attorney, Agent, or Firm* — Muncy, Geissler, Olds & Lowe, PLLC

(57) ABSTRACT

A positioning method for orthodontic appliance and structure, mainly provided with base units molded by plastic injection. During the fabricating process, a crossed reference line is first drawn on a dental mold of the patient, after heating, the orthodontic appliance is embedded to the base unit, and a flexible member is used to bind and fixedly position the orthodontic appliance. Each of the aforementioned base units together with the orthodontic appliance is attached to the dental mold, and then light curing composite resin is attached to each of the base units. Accordingly, after applying an adhesive layer to each of the orthodontic appliances, each of the series connected base units together with the orthodontic appliances bound to the base units is directly attached to the respective teeth portion of the patient requiring straightening, thereby enabling fitting of orthodontic appliances to be more convenient and providing a more efficient fabricating process.

5 Claims, 8 Drawing Sheets

POSITIONING METHOD FOR ORTHODONTIC APPLIANCE AND STRUCTURE THEREOF

BACKGROUND OF THE INVENTION (a) Field of the Invention

The present invention relates to a positioning method for orthodontic appliance and structure thereof, and more particularly to a positioning method and structure which enables fitting of orthodontic appliances to be more convenient and more efficient, thereby reducing fitting cost.

(b) Description of the Prior Art

In general, when straightening crooked teeth, orthodontic appliances are normally attached to the surfaces the teeth, after which each of the orthodontic appliances are tightly connected. Traditional fitting methods of orthodontic appliances roughly follow the following steps:

1. First fabricating a dental mold according to the condition of the teeth of the patient.
2. Drawing a cross line on the dental mold, and coating the inner edge with wax material.
3. Aligning the orthodontic appliance with the inner edge of the dental mold according to the cross line, and then forming a basic unit for a single tooth using powder molding.
4. Binding the basic unit and the orthodontic appliance using a flexible member.
5. When fitting, applying an adhesive to the orthodontic appliances, and attaching one by one to the teeth of the patient.
6. Removing the flexible members and taking off the basic units, thereby enabling the orthodontic appliances to be fixed to the dental surface, and then connecting each of the orthodontic appliances to complete the fitting.

The aforementioned fitting method of orthodontic appliances of the prior art can only be used according to the teeth of an individual patient; moreover, a professional dental lab technician must match up and fabricate the basic units, and the entire fabricating and fitting process is labor intensive and time consuming, efficiency is poor, and cost of fitting is relatively high, thus increasing the economic burden on the patient. In light of this, the applicant, having accumulated years of experience in related arts, and through continuous research and experimentation, has endeavored to provide an improved positioning method for orthodontic appliance and structure thereof, with the intention of enabling fitting of orthodontic appliances to be more convenient and providing a more efficient fabricating process.

SUMMARY OF THE INVENTION

A primary objective of the present invention is to provide a positioning method for orthodontic appliance and structure thereof, enabling fitting of the orthodontic appliance to be more convenient and more efficient, thereby reducing cost of fitting.

The aforementioned positioning method for orthodontic appliance uses base units molded by plastic injection, and during the fabricating process, a crossed reference line is first drawn on a dental mold of the patient, after heating, the orthodontic appliance is embedded to the base unit, and a flexible member is used to bind and fixedly position the orthodontic appliance. Each of the aforementioned base units together with the orthodontic appliance thereof is attached to the dental mold, and after appropriately adjusting the positions of the orthodontic appliances, light curing composite resin is attached to each of the base units, enabling the light curing composite resin to mutually connect each of the base units. Accordingly, after applying an adhesive layer to each of the orthodontic appliances, each of the series connected base units together with the orthodontic appliances bound to the base units is directly attached to the respective teeth portion of the patient requiring straightening, thereby enabling fitting of orthodontic appliances to be more convenient and providing a more efficient fabricating process.

The aforementioned positioning structure of an orthodontic appliance comprises a base unit fabricated from a horizontal hook portion and a vertical portion based on different teeth portions and different forms of orthodontic appliance, with a serial number for the teeth portion being marked on the horizontal hook portion of each of the base units. The vertical portion is fitted with a transverse positioning channel, and a vertical alignment groove is provided in a central position of the vertical portion, thereby forming crossed reference lines. After heating, the orthodontic appliance is embedded to the vertical portion of the base unit, and bound tight thereto using a flexible member.

To enable a further understanding of said objectives and the technological methods of the invention herein, a brief description of the drawings is provided below followed by a detailed description of the preferred embodiments.

DETAILED DESCRIPTION OF THE PREFERRED EMBODIMENTS

Figure 1:
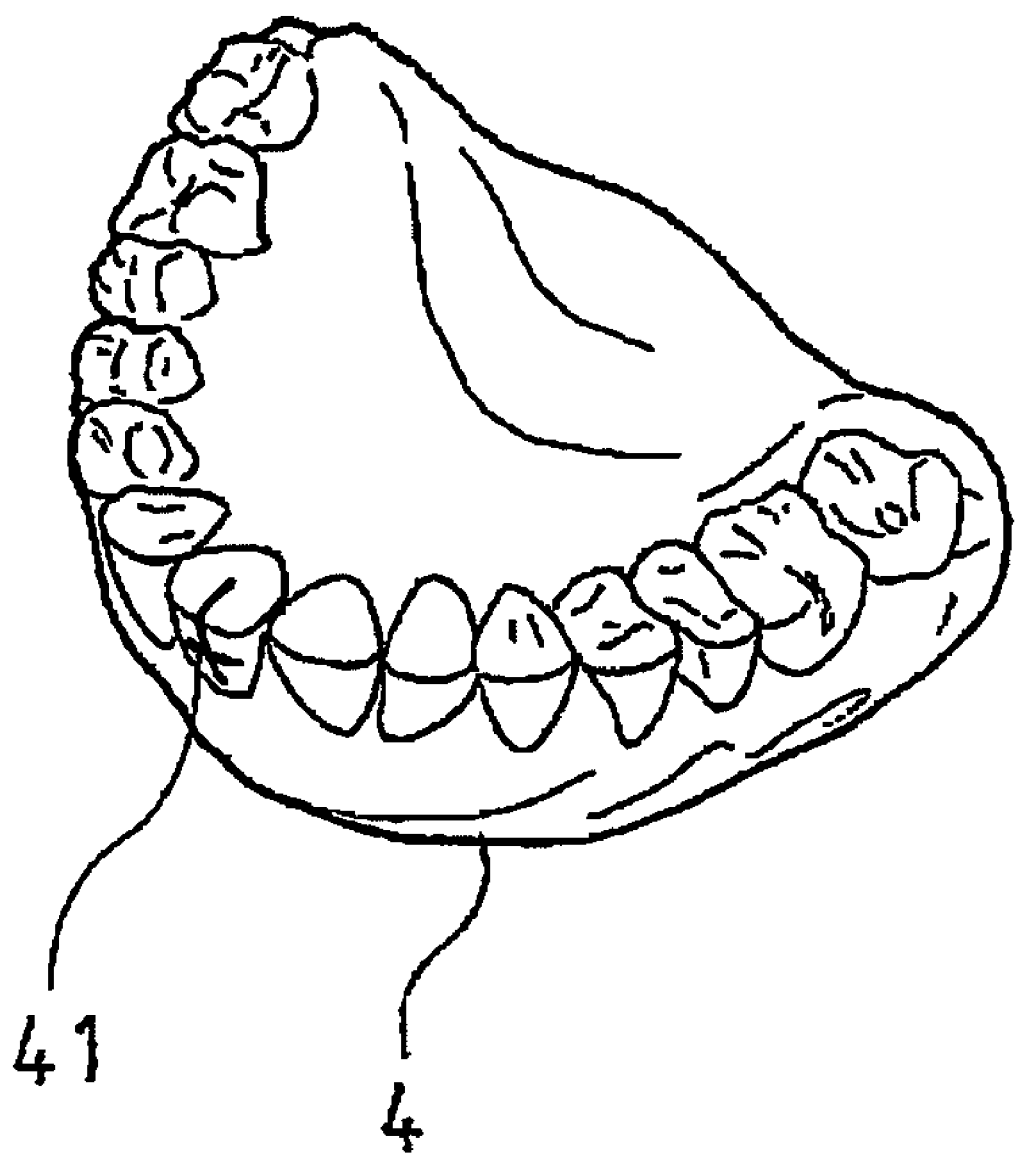
FIG. 1 is an implementation drawing depicting the fabricating process on a dental mold according to the present invention.
Figure 1A:
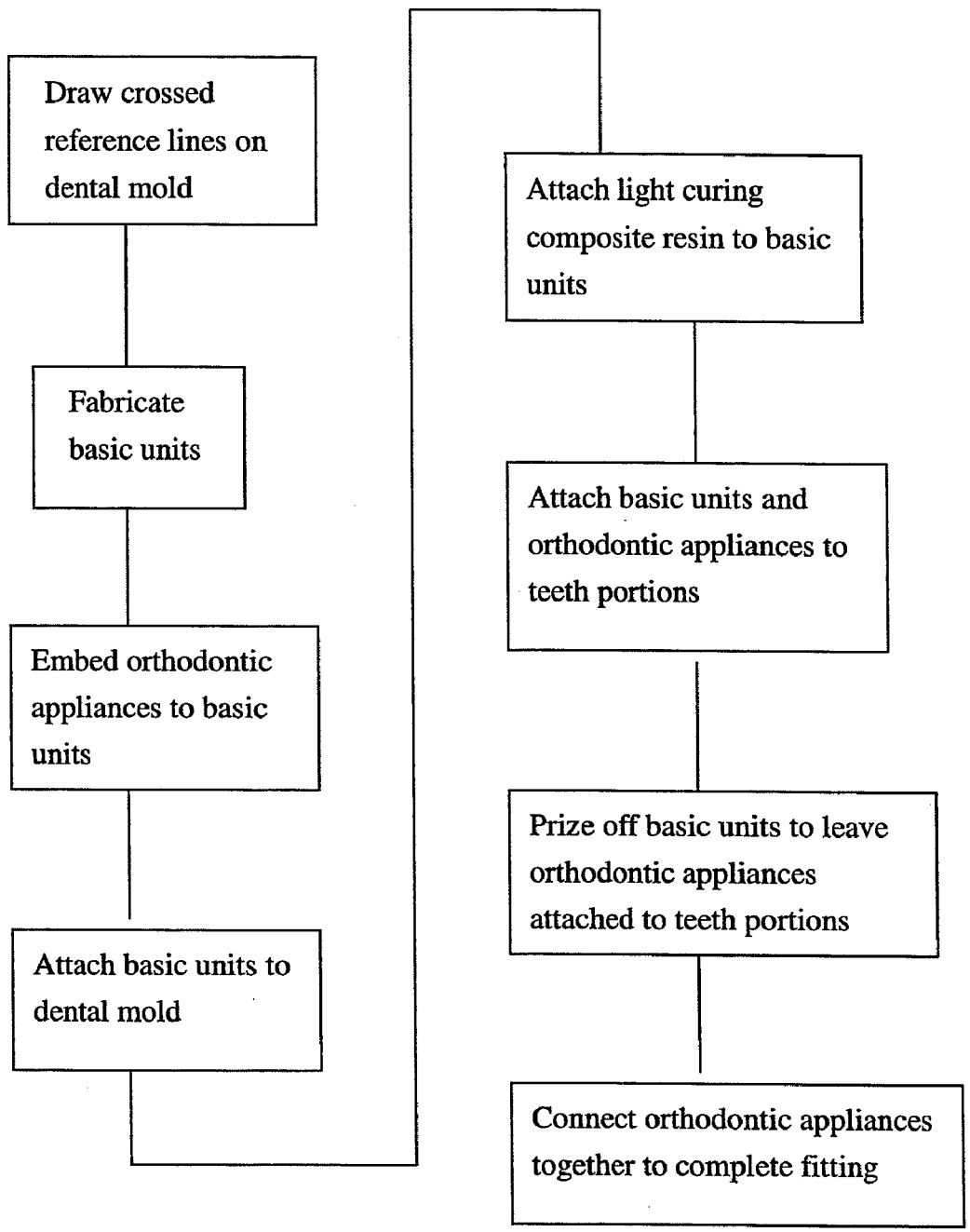
FIG. 1A is a flow chart depicting the fabricating process according to the present invention.

Referring together to FIG. 1 and FIGS. 1A to FIG. 7, which show the entire fabricating and fitting process of the present invention, primarily comprising the following steps:

1. Fabricating a dental mold 4 according to the dental profile of the patient, and drawing crossed reference lines 41 on the dental mold 4 of the patient (see FIG. 1) using a specific instrument.

2. Fabricating different base units 1 using plastic injection molding means based on different teeth portions and different forms of orthodontic appliance, wherein each of the base units 1 comprises a horizontal hook portion 11 and a vertical portion 12 extending downward from the horizontal hook portion 11. In which the vertical portion 12 is provided with a transverse positioning channel 121 at an appropriate position thereof, and a vertical alignment groove 122 is provided in a central position of the vertical portion 12, thereby forming crossed reference lines. (see FIG. 2).

3. Allocating the vertical portion 12 of each of the base units 1 with a serial number 111 according to each of the different teeth portions (see FIG. 2).

Figure 2:
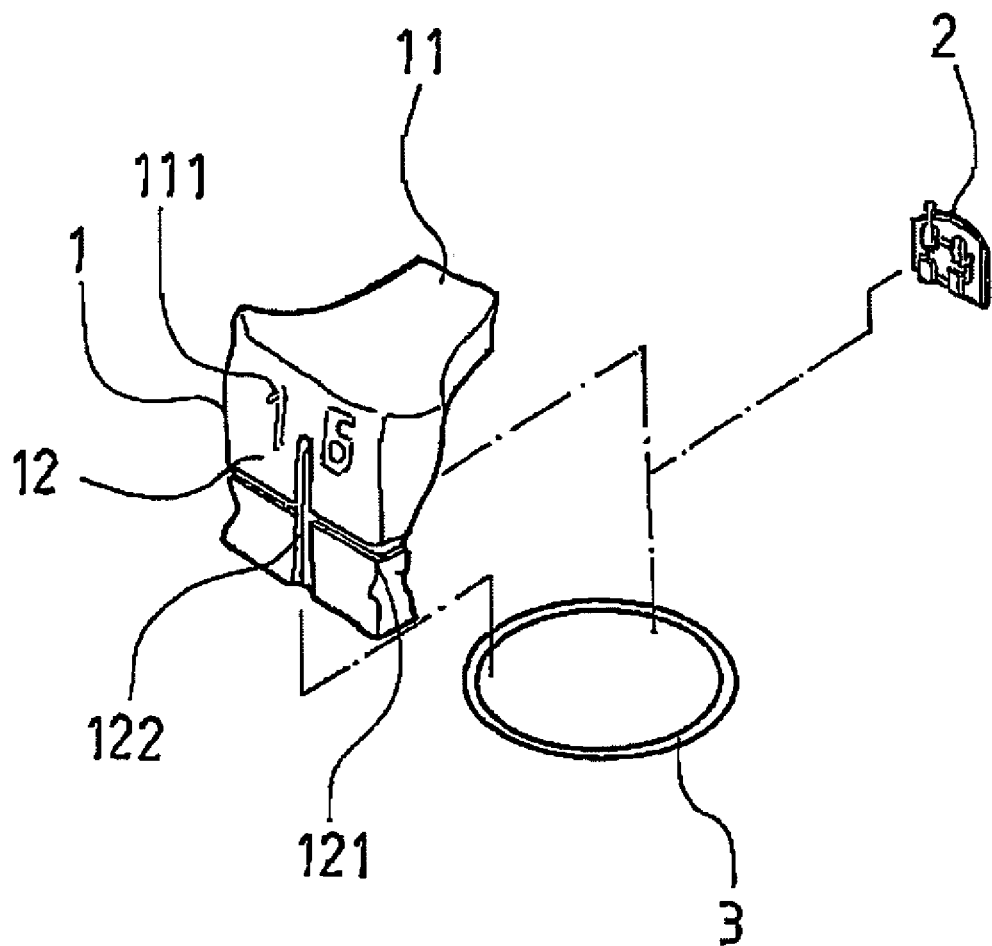
FIG. 2, FIG. 2A are exploded elevational views of the present invention.
Figure 2A:
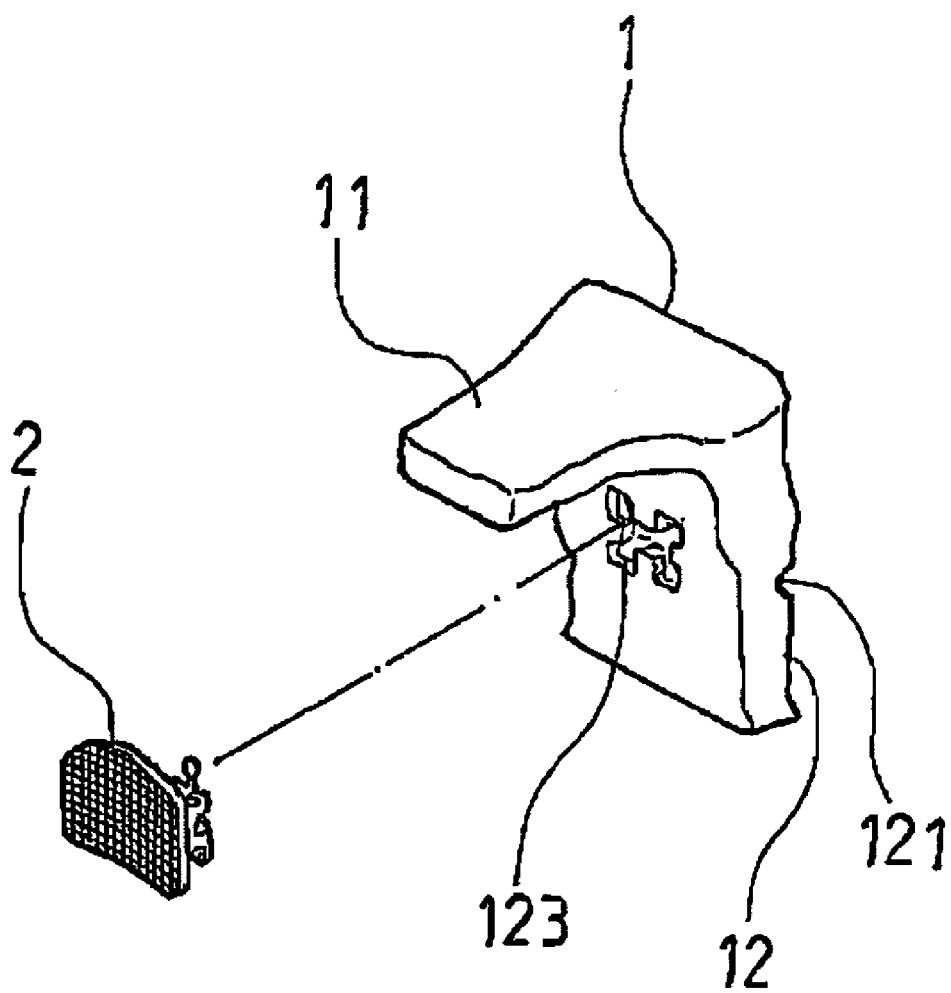

4. After heating, embedding an orthodontic appliance 2 into a rear edge of the vertical portion 12 of the base unit 1, thereby enabling the base unit 1 to form a stabilizing base 123 for the orthodontic appliance 2 according to the shape of the orthodontic appliance 2, and a flexible member 3 is used to bind and fixedly position the orthodontic appliance 2 along the positioning channel 121 (see FIG. 2 and FIG. 2A).

Figure 3:
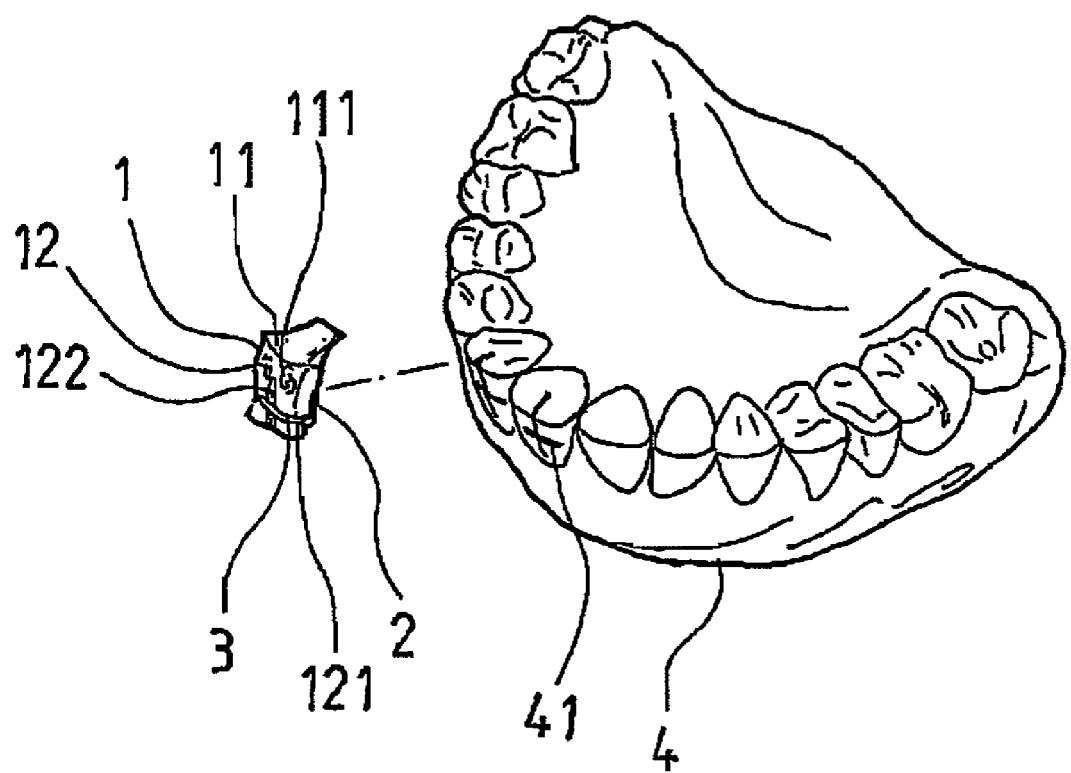
FIG. 3, FIG. 3A are elevational views of an embodiment depicting a first step in the fabricating process according to the present invention.
Figure 3A:
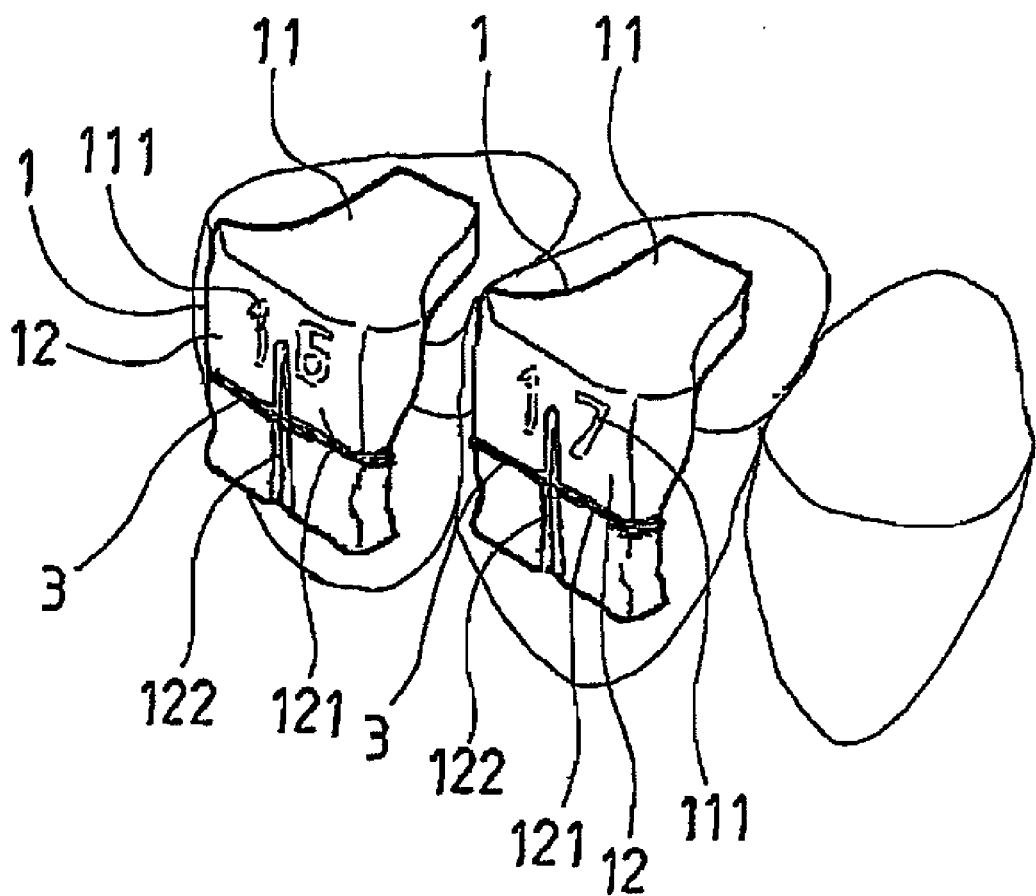
Figure 4:
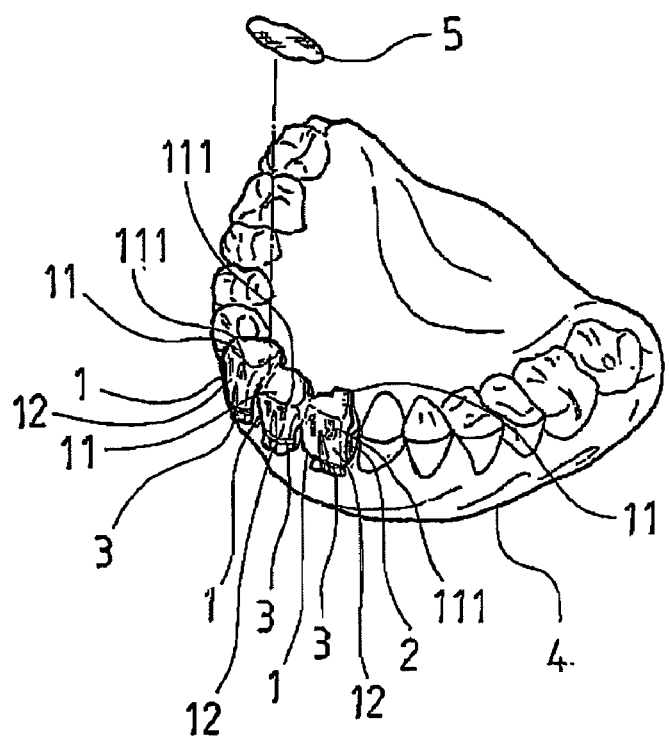
FIG. 4 is an elevational view of the embodiment depicting a second step in the fabricating process according to the present invention.
Figure 5:
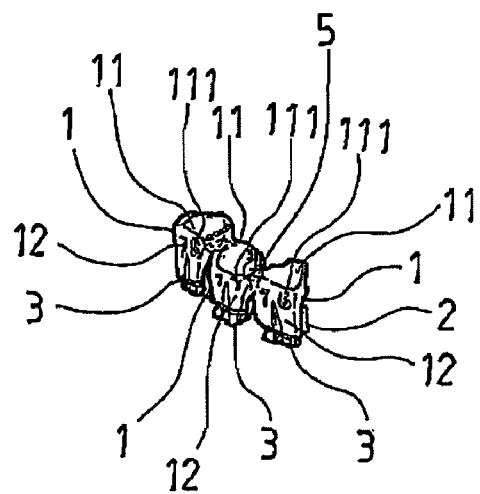
FIG. 5 is an elevational view of the embodiment depicting a third step in the fabricating process according to the present invention.
Figure 6:
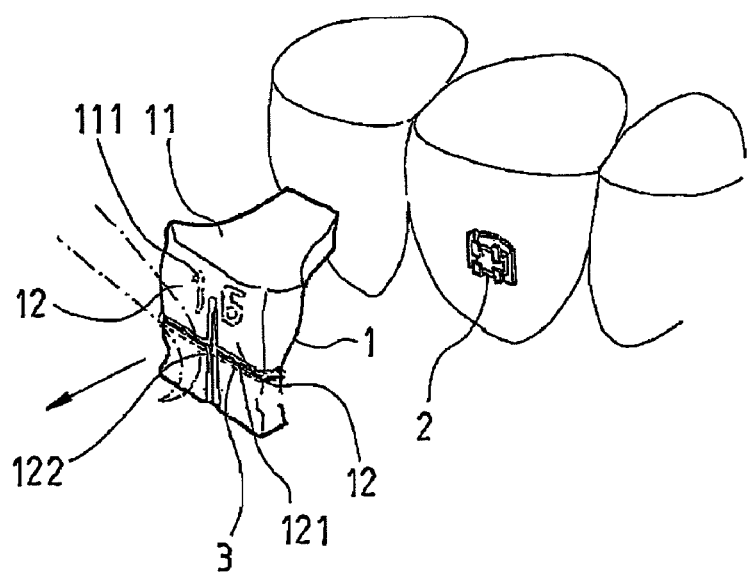
FIG. 6 is an implementation drawing depicting the fitting of a base unit according to the present invention.
Figure 7:
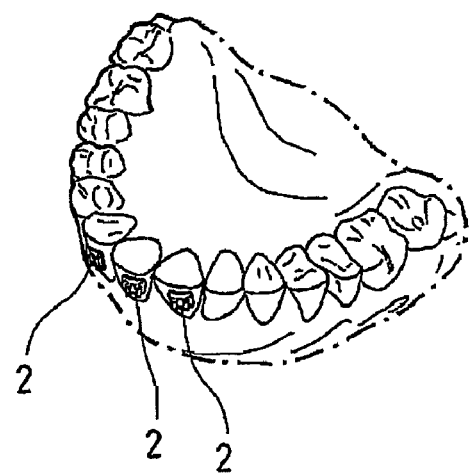
FIG. 7 is an implementation drawing depicting an orthodontic appliance fixed to a teeth portion according to the present invention.

5. Attaching each of the aforementioned base units 1 together with the respective orthodontic appliance 2 bound to the base unit 1 to the dental mold 4 (see FIG. 3 and FIG. 3A), respectively aligning with the crossed reference lines of the dental mold 4 using the crossed reference lines formed by the positioning channel 121 and the alignment groove 122 of the vertical portion 12, after which the positions of the orthodontic appliances 2 are appropriately adjusted.

6. Attaching light curing composite resin 5 to each of the aforementioned base units 1 to enable the inner edge of the light curing composite resin 5 to form occlusal surfaces, and then mutually connecting each of the base units using the same light curing composite resin 5 (see FIG. 4).

7. Series connected base units 1 are thus formed after the light curing composite resin 5 hardens.

8. Taking off each of the series connected base units together with the respective orthodontic appliance 2 bound to the base unit 1 from the dental mold 4 (see FIG. 5).

9. After applying an adhesive layer to each of the orthodontic appliances 2, directly attaching each of the series connected base units 1 together with the corresponding orthodontic appliance 2 bound to the base unit 1 to each respective teeth portion of the patient requiring straightening.

10. After the adhesive layer is fixed, the flexible member 3 bound to the each of the base units 1 is prized off using a specific tool, and each of the base units 1 is dismantled from the respective orthodontic appliance 2 (see FIG. 6).

11. After dismantling the base units 1, the orthodontic appliances 2 remain respectively fixed to the surfaces of the teeth portions requiring straightening (see FIG. 7), whereupon the dentist is able to tightly connect each of the orthodontic appliances 2, thus completing the fitting process of the orthodontic appliances 2.

The aforementioned positioning method for orthodontic appliance and structure thereof of the present invention is provided with at least the following advantages compared to traditional fitting methods:

1. Eliminates the troublesome matter of fabricating base units by a technician, enabling direct use by the dentist, thereby saving time on fitting, and increasing work efficiency.

2. Because the procedure of fabricating base units by a technician is eliminated, thus, cost of fitting and economic burden on the patient is reduced.

3. During fitting, the series connected base units 1 and the orthodontic appliances 2 are directly fitted to the teeth of the patient, thereby enabling fast and accurate fitting time,.

In conclusion, the present invention uses prefabricated base units, in conjunction with orthodontic appliances bound to the base units, to enable fitting of orthodontic appliances to be more convenient and more efficient, thereby reducing fitting cost. The present invention provides a practical design, and is indeed a novel appliance. Accordingly, a new patent application is proposed herein.

It is of course to be understood that the embodiments described herein are merely illustrative of the principles of the invention and that a wide variety of modifications thereto may be effected by persons skilled in the art without departing from the spirit and scope of the invention as set forth in the following claims.

What is claimed is:

1. A positioning method for orthodontic appliance and structure thereof, comprising the steps of:
   a), fabricating a dental mold according to the dental profile of the patient, and drawing crossed reference lines on the dental mold using a specific instrument;
   b), fabricating different base units based on different teeth portions and different forms of orthodontic appliance, wherein each of the base units is provided with crossed reference lines, and each of the base units is allocated with a serial number;
   c), heating the orthodontic appliance;
   d), after heating the orthodontic appliance, embedding the heated orthodontic appliance to the base unit, and binding and fixedly positioning the orthodontic appliance using a flexible member, thereby causing the base unit to form a stabilizing base for the orthodontic appliance according to the shape of the orthodontic appliance;
   e), attaching each of the base units together with the respective orthodontic appliance bound to the base unit to the dental mold, aligning with the crossed reference lines of the dental mold, and appropriately adjusting the positions of the orthodontic appliances;
   f), attaching light curing composite resin to each of the base units to enable the inner edge of the light curing composite resin to form occlusal surfaces, and then mutually connecting each of the base units using the same light curing composite resin;
   g), forming series connected base units after coagulation of the light curing composite resin;
   h), taking off each of the series connected base units together with the respective orthodontic appliance bound to the base unit from the dental mold;
   i), directly attaching each of the series connected base units together with the corresponding orthodontic appliance bound to the base unit to each respective teeth portion of the patient requiring straightening after applying an adhesive layer to each of the orthodontic appliances;
   j), after attachment of the series connected base units together with the corresponding orthodontic appliance bound to the base unit to each respective teeth portion, removing the flexible members and base units by prying off of the flexible member bound to each of the base units using a specific tool after the adhesive layer is fixed, and after removing the flexible member from the base unit, dismantling each of the base units from the respective orthodontic appliance, thereby fixing the orthodontic appliances to the surfaces of the teeth portions requiring straightening, whereupon each of the orthodontic appliances are tightly connected, thus completing the fitting process of the orthodontic appliances.

2. The positioning method for orthodontic appliance and structure thereof according to claim 1, wherein the base units are fabricated using plastic injection molding means.

3. The positioning method for orthodontic appliance and structure thereof according to claim 1, wherein the base unit comprises a horizontal hook portion and a vertical portion extending downward from the horizontal hook portion, thereby enabling the horizontal hook portion to be used to hold onto the dental mold and the teeth portion of the patient.

4. The positioning method for orthodontic appliance and structure thereof according to claim 3, wherein the vertical portion of the base unit is provided with a transverse positioning channel and a vertical alignment groove, thereby forming crossed reference lines.

5. The positioning method for orthodontic appliance and structure thereof according to claim 1, wherein step h further includes directly grasping the series connected base units before removing the series connected base units and respective orthodontic appliance bound to the base unit from the mold.

* * * * *